United States Patent [19]

Tong

[11] Patent Number: 5,686,062

[45] Date of Patent: Nov. 11, 1997

[54] ACRYLIC HAIR FIXATIVES AND METHODS OF MAKING SAME

[75] Inventor: Quinn Kun Tong, Belle Mead, N.J.

[73] Assignee: National Starch and Chemical Investment Holding Corporation, Wilmington, Del.

[21] Appl. No.: 581,659

[22] Filed: Dec. 29, 1995

[51] Int. Cl.$^6$ ..................................................... A61K 7/00
[52] U.S. Cl. ........................................... 424/47; 424/70.16
[58] Field of Search ..................................... 424/47, 70.16

[56] References Cited

U.S. PATENT DOCUMENTS

| | | | |
|---|---|---|---|
| 2,996,471 | 8/1961 | Reiter et al. | 260/33.4 |
| 3,574,822 | 4/1971 | Shepherd et al. | 424/47 |
| 3,660,561 | 5/1972 | Shepherd et al. | 424/47 |
| 3,810,977 | 5/1974 | Levine et al. | 424/47 |
| 3,927,199 | 12/1975 | Micchelli et al. | 424/47 |
| 4,192,861 | 3/1980 | Micchelli et al. | 424/47 |
| 4,196,190 | 4/1980 | Gehman et al. | 424/47 |
| 4,261,972 | 4/1981 | Nandagiri et al. | 424/47 |
| 4,315,910 | 2/1982 | Nowak, Jr. et al. | 424/47 |
| 4,767,613 | 8/1988 | Nuber et al. | 424/47 |
| 4,798,721 | 1/1989 | Yahagi et al. | 424/70 |
| 4,842,852 | 6/1989 | Nowak, Jr. et al. | 424/71 |
| 4,961,921 | 10/1990 | Chuang et al. | 424/47 |
| 4,985,239 | 1/1991 | Yahagi et al. | 424/70 |
| 5,021,238 | 6/1991 | Martino et al. | 424/47 |
| 5,068,099 | 11/1991 | Sramek | 424/47 |
| 5,094,838 | 3/1992 | Benson et al. | 424/47 |
| 5,158,762 | 10/1992 | Pierce | 424/47 |
| 5,164,177 | 11/1992 | Bhatt et al. | 424/47 |
| 5,176,898 | 1/1993 | Goldberg et al. | 424/47 |
| 5,304,368 | 4/1994 | Shernov et al. | 424/47 |
| 5,374,420 | 12/1994 | Gerstein | 424/70.11 |
| 5,413,775 | 5/1995 | Hatfield et al. | 424/47 |

FOREIGN PATENT DOCUMENTS

| | | |
|---|---|---|
| 677267 | 9/1966 | Belgium . |
| 274086 | 7/1988 | European Pat. Off. . |
| 445714 | 9/1991 | European Pat. Off. . |
| 2697160 | 10/1992 | France . |
| 2098226 | 11/1982 | United Kingdom . |
| 2136689 | 9/1984 | United Kingdom . |
| WO93/09757 | 5/1993 | WIPO . |
| WO94/02112 | 2/1994 | WIPO . |

*Primary Examiner*—Margaret W. Glass
*Attorney, Agent, or Firm*—William K. Wissing

[57] ABSTRACT

Methods of preparing a homogeneous solution of a partially-neutralized acrylic polymer in a solvent system comprising greater than 50 weight percent water and 0 to less than 50 weight percent of an organic solvent are disclosed, wherein the homogeneous solution of the partially-neutralized acrylic polymer has pH and viscosity which are effective for use in acrylic hair fixative compositions. Also disclosed are methods of preparing an acrylic hair fixative composition, which methods include preparing the homogeneous solution of the partially-neutralized acrylic polymer as above. Also disclosed are acrylic hair fixative compositions which contain the partially-neutralized acrylic polymer, water and, optionally, one or more of an organic solvent, a propellant and an emulsifier.

72 Claims, No Drawings

ACRYLIC HAIR FIXATIVES AND METHODS OF MAKING SAME

FIELD OF THE INVENTION

The present invention relates to hair fixative compositions which comprise a homogeneous solution of a partially-neutralized acrylic polymer in a solvent system where water is the primary solvent and methods for making the homogeneous solution of the partially-neutralized acrylic polymer and the hair fixative compositions containing such solution.

BACKGROUND OF THE INVENTION

In order to be effective in hair fixative compositions such as aerosol or nonaerosol hair sprays, mousses and lotions, the film forming resins utilized therein, as well as the films formed therefrom, must meet certain requirements. The resins used in such compositions should be soluble in the solvent systems used to prepare the hair fixative compositions. Particularly in hair fixative compositions containing low levels of volatile organic compounds (VOC), where water is used as the primary solvent, the resin should be water-soluble in order to prepare aqueous solutions of the resins. The resins also must be compatible with the solvent/propellant system in the aerosol application in order to provide the aerosol fixatives with adequate spray properties. In addition, the films cast from such compositions must be either water-soluble or water-dispersible in order to facilitate the easy removal from the user's hair.

One class of resins used in hair fixatives are acrylic polymers which contain carboxylic acid groups. Exemplary of such acrylic polymer resins containing carboxylic acid groups include without limitation the copolymers of n-tert-octylacrylamide, methyl methacrylate, hydroxypropyl methacrylate, acrylic acid and t-butyl aminoethyl methacrylate, available from National Starch and Chemical Company under the Amphomer and the Amphomer LV-71 trade names; copolymers of n-tert-octylacrylamide, methyl methacrylate, acrylic acid and t-butyl aminoethyl methacrylate, available from National Starch and Chemical Company under the Lovocryl trade name; and copolymers of vinyl acetate, crotonic acid and a vinyl ester of an alpha-branched saturated aliphatic monocarboxylic acid containing from 5 to 10 carbon atoms in the carboxylic acid moiety, available from National Starch and Chemical Company under the Resyn trade name.

Such acrylic copolymers are known to be soluble in organic solvents such as ethanol and typically are used in hair fixative compositions which utilize an organic solvent as the sole or primary solvent. Such acrylic polymers, it is suggested, are known to be water-insoluble unless their carboxylic acid groups are neutralized by alkaline reagents to a level of at least 90% on a molar basis. If the neutralization on a molar basis is lower than 90%, the films derived from those hair fixative compositions utilizing the acrylic polymers generally should not be water-soluble and the fixative resins should not be removable readily from the hair. Accordingly, if such acrylic polymers are intended to be used in formulating low VOC hair fixative compositions, it is taught generally to neutralize the carboxylic acid content to at least 90 mole % to enhance the water-solubility of the resin and to ensure the easy removal of the resin from the hair. For example, in International Publication No. WO/93/09757, in hair fixative compositions containing water as the primary solvent and a propellant, 100 mole % of the carboxylic functionality on the acrylic polymers are neutralized.

In addition to being removable readily from the hair, the resin also must be compatible with the solvent/propellant system used in aerosol hair fixatives. The general water-insolubility of such acrylic polymers creates specific problems with respect to hair fixative compositions which contain water as the sole or primary solvent and a propellant, under pressure, such as low VOC aerosol sprays. In such aerosol hair spray applications, a uniform, fine mist or spray is desirable to effectively distribute the hair fixative on the hair. The high levels of neutralization required to provide solubility of the resin in water, thereby providing removability of the film from hair, results in increased viscosity of the hair fixative compositions. The high viscosity results in undesirable spray aesthetics, such as a narrow spray cone, large spray droplets, spitting, foaming and forceful spray, for example. Therefore, as indicated above, the carboxylic acid functionality of the acrylic polymers are neutralized prior to their incorporation into such low VOC hair fixatives, generally at a level from 90% to 100% on a molar basis.

Neutralization methods generally are known where such acrylic polymers are neutralized prior to being used in hair fixative compositions. U.S. Pat. No. 3,927,199 discloses hair fixative compositions containing acrylic copolymers and organic solvent as the primary solvent. In order to meet the removability requirement of a hair fixative, the acrylic resins may be partially neutralized prior to their being incorporated into the hair fixing formulations, thus permitting them to be removed from the hair merely be rinsing with water. The neutralization may be accomplished by reacting the polymer in the form of a solution in an organic solvent, with or without added water, with a concentration of an alkaline reagent (neutralizing agent) which is equivalent on a molar basis to a minimum of about 50% of the available carboxyl groups present on the polymer. The above method can be conducted in the presence of organic solvents such as ethanol. Methods of neutralizing the acrylic polymer in water as the primary solvent are not disclosed or discussed.

U.S. Pat. No. 4,315,910 discloses acrylic polymers for use in aerosol hair fixatives. Small amounts of water, i.e., 1 to 15%, preferably 3 to 8%, are taught to improve the shelf stability and solubility of the polymer. The carboxylic acid groups of the copolymer require neutralization to enhance the water-solubility of the resin to ensure the easy removal of the resin from the hair. The neutralization of acrylic polymers is accomplished by first reacting a solution of the polymer in an organic solvent, with or without added water, with a concentration of an alkaline reagent which is effective to neutralize 70 to 100 mole percent of the carboxyl groups. The appropriate amount of water (not to exceed 15 percent w/w) is added then to the organic solvent solution of the neutralized resin prior to charging the formulation into the aerosol container. The propellant used in the aerosol applications is a hydrocarbon or carbon dioxide.

U.S. Pat. No. 4,261,972 discloses pressurized hair spray compositions which may contain a broad range of acrylic resin hair fixatives and from 2 to 30 percent by weight of water. The acid groups of the acrylic resins are neutralized from 50 to 100 percent with an organic base. When the water content is above 30 percent, the product is dispensed as a foam, which is not desired. The propellants used in these aerosol applications are hydrocarbons.

There has been an ongoing effort in the hair care industry to significantly reduce or eliminate organic solvents in hair fixatives. Additionally, regulatory bodies push to lower the level of VOC, which include ethanol and equivalent hair fixative solvents, in various industries, including hair care products. As the art suggests, increased levels of water, i.e., up to 30 weight percent, are sought to correct certain deficiencies of organic solvent systems, such as flammability and plasticization.

While the methods of neutralization noted above may be used where an organic solvent is the primary or sole solvent, neutralization where water is the primary or sole solvent used to prepare the hair fixatives is problematic. In the known methods, the dry acrylic polymer is dissolved in the organic solvent prior to being incorporated into the hair fixative, which may include small amounts of water blended therein. However, where water is the primary solvent, one must first determine how to dissolve the water-insoluble, unneutralized polymer in the water solvent. Thus, methods of preparing hair fixative compositions which significantly reduce or eliminate organic solvents in the hair fixative compositions are sought.

The present invention provides such methods for preparing low VOC, acrylic hair fixative compositions, which methods significantly reduce or eliminate organic solvents from methods for making the hair fixatives and the hair fixatives produced therefrom.

SUMMARY OF THE INVENTION

The present invention is directed to methods of preparing a homogeneous solution of a partially-neutralized acrylic polymer in a solvent system comprising greater than 50 weight percent water and 0 to less than 50 weight percent of an organic solvent, wherein the homogeneous solution of the partially-neutralized acrylic polymer has pH and viscosity which are effective for use in acrylic hair fixative compositions. The invention is also directed to methods of preparing an acrylic hair fixative composition, which methods include preparing the homogeneous solution of the partially-neutralized acrylic polymer as above. The invention is also directed to acrylic hair fixative compositions comprising the partially-neutralized acrylic polymer, water and, optionally, one or more of an organic solvent, a propellant and an emulsifier.

DETAILED DESCRIPTION OF THE INVENTION

Acrylic polymer, as used herein, is intended to include those polymers which contain at least one α-β ethylenically unsaturated acidic monomer containing one or more carboxylic groups. Preferred acrylic, film forming polymers utilized as resins in the hair fixative compositions of this invention comprise polymers containing the residue of at least one acidic monomer containing one or more carboxyl groups, and at least one monomer selected from a group of monomers which are copolymerizable with the acidic monomers, hereinafter referred to as a copolymerizable monomer.

The following list of monomers are representative of the applicable acrylic, acidic film forming monomers which contain at least one carboxylic acid group: acrylic acid, methacrylic acid, crotonic acid, itaconic acid, maleic acid, fumaric acid and the $C_1$–$C_4$ alkyl half esters of maleic and fumaric acids, such as methyl hydrogen maleate and butyl hydrogen fumarate, as well as any other acidic monomers which are capable of being copolymerized with the particular polymer system whose use is desired by the practitioner. As is known to those skilled in the art, the acidic monomer must be chosen so as to be readily polymerizable with the selected polymer system.

In order to modify or enhance certain properties of the acrylic polymer, for example, adherence to the hair, water-solubility, hardness, flexibility, antistatic properties, and the like, the practitioner may utilize one or more copolymerizable monomer in the preparation of the polymeric resins of this invention. Among these copolymerizable monomers are the acrylic and methacrylic acid esters of aliphatic alcohols having from 1 to 12 carbon atoms such as methyl, ethyl, propyl, butyl, octyl and lauryl alcohols; hydroxyalkyl esters of acrylic and methacrylic acids such as hydroxypropyl acrylate and methacrylate, hydroxybutyl acrylate and methacrylate, hydroxystearyl acrylate and methacrylate and hydroxyethyl acrylate and methacrylate; $C_1$–$C_4$ alkyl amino $C_2$–$C_4$ alkyl esters of acrylic and methacrylic acids such as N,N'-dimethylaminoethyl methacrylate, N-tert-butylaminoethyl methacrylate and the quaternization product of dimethylaminoethyl methacrylate and dimethyl sulfate, diethyl sulfate and the like; diacetone acrylamide; vinyl esters such as vinyl acetate, vinyl neodecanoate and vinyl propionate; styrene monomers such as styrene and alpha-methyl styrene; and N-substituted acrylamides or methacrylamides substituted with alkyl groups containing from 2 to 12 carbon atoms. Among the applicable acrylamides and methacrylamides are included N-ethyl acrylamide, N-tertiary-butyl acrylamide, N-n-octyl acrylamide, N-tertiary-octyl acrylamide, N-decyl acrylamide and N-dodecyl acrylamide, as well as the corresponding methacrylamides.

In order to provide resins which will function efficiently in the novel hair fixative compositions of this invention, the acrylic polymer may comprise the residue of from 0 to about 60 weight percent of the N-substituted acrylamide and/or N-substituted methacrylamide, from about 8 to about 25 weight percent of the acidic monomer, and 0 to about 90 weight percent of at least one copolymerizable monomer other than the N-substituted acrylamide or N-substituted methacrylamide. Preferably, the polymer comprises the residue of from about 10 to about 22 weight percent of the acidic monomer, from about 35 to about 55 weight percent of an N-alkyl acrylamide and/or N-alkyl methacrylamide monomer and from about 25 to about 80 weight percent of the copolymerizable monomer other than the N-alkyl acrylamide or N-alkyl methacrylamide. Most preferably, the polymer comprises the residue of from about 15 to about 20 weight percent of the acidic monomer, from about 38 to about 52 weight percent of the N-alkyl acrylamide and/or N-alkyl methacrylamide and from about 30 to about 50 weight percent of the copolymerizable monomer other than the N-alkyl acrylamide or N-alkyl methacrylamide. All monomer weight percents are based on the total weight of monomers used to prepare the polymers.

As for the actual preparation of the acrylic polymers, there may be employed any of the usual vinyl polymerization methods which are well known to those skilled in the art and which are particularly suited for the polymer whose preparation is desired. Thus, the polymers may be prepared by means of free radical initiated processes utilizing bulk, suspension, solution, or emulsion polymerization techniques. The polymers may, if desired, be converted into relatively large particles known as beads or pearls by dispersing the solution polymerized polymer in water and thereafter driving off the solvent followed by separating and drying the particles.

The acrylic polymer resins are partially neutralized in a solvent system wherein water is the primary solvent, such that a homogeneous solution of the partially-neutralized acrylic polymer in the solvent system is formed. By primary solvent, it is meant that water is always the major constituent of the solvent system. That is to say, the solvent system always contains greater than 50 weight percent of the water, preferably greater than 60 weight percent of the water and even more preferably greater than 75 weight percent of the water, based on the total weight of the solvent system. The solvent system may further include organic solvents such as ethanol, isopropanol, acetone, ethylene glycol dimethyl ether (EGDME) and methyl ethyl ketone.

In preparing the homogeneous solution of the partially-neutralized acrylic polymer, a two-step process is utilized wherein the acrylic polymer first is neutralized in the solvent system with a neutralizing base to form a homogeneous solution of the neutralized acrylic polymer and then acid is added to the solution of the neutralized acrylic polymer under conditions effective to form a homogeneous solution of the partially-neutralized acrylic polymer in the solvent system. Neutralized acrylic polymer, as used herein, is used to denote the acrylic polymer after it has been neutralized with the neutralizing base, but before the acid is added to the solution of the neutralized acrylic polymer. Partially-neutralized acrylic polymer, as used herein, is used to denote the acrylic polymer after both the neutralization with base and the addition of acid has been completed.

In certain embodiments, the acrylic polymer, typically in powder form, is combined with the solvent system and an amount of the neutralizing base which is effective to neutralize the acrylic polymer to the extent that the neutralized acrylic polymer is soluble in the solvent system, thereby forming a homogeneous solution of the neutralized acrylic polymer in the solvent system. Preferably, the neutralizing base is added to the solvent system in predetermined effective amounts. The acrylic polymer is then added to the mixture of the solvent system and the neutralizing agent with stirring until the homogeneous solution of the neutralized acrylic polymer is formed. Dissolution of the neutralized acrylic polymer in the solvent system preferably is completed without the necessity of inputting energy into the system, such as high shear mixing or heating. Applicable neutralizing bases include, without limitation, sodium and potassium hydroxide, ammonia, primary, secondary and tertiary amines, alkanolamines and hydroxyamines, such as 2-amino-2-methyl-propanol and 2-amino-2-methyl-1,3-propanediol, respectively. The effective amount of the neutralizing base which is utilized will depend on the particular level and type of acidic monomer used to prepare the acrylic polymer. The effective amount of neutralizing base may be a molar ratio of base to the carboxyl groups contained in the acrylic polymer which is greater than or equal to 0.9:1, preferably, from about 0.9:1 to about 2:1, and more preferably from about 1:1 to about 1.5:1. The solution of the neutralized acrylic polymer must be homogeneous and must be stable from phase separation and precipitation. The pH of the solution of the neutralized acrylic polymer generally will be about 7 or greater, but typically less than 10.

After the homogeneous solution of the neutralized acrylic polymer is prepared a water-soluble acid is added to the solution of neutralized acrylic polymer to reduce the level of neutralization of the neutralized acrylic polymer, thereby forming a partially-neutralized acrylic polymer. The acid is added in an amount and under conditions which are effective to provide a homogeneous solution of the partially-neutralized acrylic polymer in the solvent system. Water-soluble acids which may be used include both organic and inorganic acids. Exemplary acids include, without limitation, acetic acid, nitric acid, phosphoric acid, sulfuric acid, hydrochloric acid, butyric acid and propionic acid. The effective amount of acid will depend on factors such as the specific acidic monomer used, the level at which the acid monomer is used, the concentration of the solution of the neutralized polymer and the relative strength of the acid. The effective amount of neutralizing base may be a molar ratio of base to the carboxyl groups contained in the acrylic polymer which is greater than or equal to 0.9:1, the effective amount of acid is a molar ratio of acid to the carboxyl groups contained in the acrylic polymer greater than or equal to 0.1:1, preferably from about 0.9:1 to about 2:1, more preferably from about 1:1 to about 1.5:1 and even more preferably from about 0.2:1 to about 0.8:1. The solution of the partially-neutralized acrylic polymer must be homogeneous and must be stable from phase separation and precipitation, and most preferably forms clear, continuous films which are redispersible in water, i.e., readily removable from hair with water and/or shampoo.

The acid is added to the solution of the neutralized acrylic polymer under conditions effective to provide the homogeneous solution of the partially-neutralized acrylic polymer. In certain embodiments, the acid should be diluted in water to a concentration effective to provide the homogeneous solution of the partially-neutralized acrylic polymer prior to the addition thereof to the solution of the neutralized acrylic polymer. Furthermore, the acid should be added over a period of time which is effective to provide the homogeneous solution of the partially-neutralized acrylic polymer. The concentration of the acid and the time period over which the acid is added will depend on factors such as the concentration of the neutralized acrylic polymer and the relative strength of the acid, for example. If either the concentration of the acid is too high or the acid, diluted or undiluted, is added too quickly, precipitation of the polymer will occur. While slight precipitation may be remedied by additional mixing, higher levels of precipitation or formation of larger polymer particles caused by improper acid addition may not be rectified, regardless of further mixing. As with the homogeneous solution of the neutralized acrylic polymer, dissolution of the partially-neutralized acrylic polymer in the solvent system preferably is completed without the necessity of inputting energy into the system, such as high shear mixing or heat. One skilled in the art, having the benefit of the disclosure herein, will be able to ascertain readily what conditions of concentration and time of acid addition would be required in order to provide the homogeneous solution of the partially-neutralized acrylic polymer.

The pH of the solution of the partially-neutralized acrylic polymer will be sufficient for use in hair fixative composition. Preferably, the pH of the solution of the partially-neutralized acrylic polymer according to the present invention will range from about 5.5 to about 8.5, more preferably from about 6 to about 8, and most preferably is about 7. The homogenous solution of the partially-neutralized acrylic polymer will contain from about 1 to about 20 weight percent of the partially-neutralized acrylic polymer, preferably from about 2 to about 15 weight percent of the partially-neutralized acrylic polymer, based on the total weight of the solvent system and the partially-neutralized acrylic polymer.

The viscosity of the solution of the partially-neutralized acrylic polymer also will be sufficient for use in hair fixative compositions. The solution viscosity is particularly critical in the case of aerosol hair fixatives, where the balancing of aerosol spray characteristics (affected by solution viscosity) versus on-hair performance of the hair fixative (affected by the presence of water) presents a problem in low VOC hair fixatives. It has been surprisingly discovered that aerosol hair fixatives according to the present invention exhibit improved spray properties while maintaining sufficient on-hair performance, compared to hair fixatives comprising neutralized acrylic polymers which have been neutralized to similar levels utilizing methods known in the art. The viscosity of a 5 percent polymer solids solution of the partially-neutralized acrylic polymer in a solvent system consisting of water and EGDME at relative weight percent of 67/33 and at 25° C. perferably will range from about 2 to about 10 cp, more preferably from about 2 to about 7 cp.

In preparing the hair fixative compositions according to the present invention, the homogeneous solution of the partially-neutralized acrylic polymer is combined with additional water and optionally a propellant or emulsifier, thereby forming the hair fixative composition. Methods of combining the ingredients are well within the knowledge of one skilled in the art of preparing hair fixative compositions.

The acrylic hair fixative composition so prepared will comprise an amount of the partially-neutralized acrylic polymer which is effective to provide the hair fixative composition with sufficient hair fixative properties, preferably from about 3 to about 10 dry weight percent based on the total weight of the hair fixative composition. The hair fixative composition may comprise from about 25 to about 97 weight percent of total water, i.e., the sum total from both the solvent system contained in the solution of the partially-neutralized acrylic polymer and the additional water added to the solution, from 0 to about 40 weight percent of the propellant and from 0 to about 15 weight percent of the emulsifier, all weight percents being based on the total weight of the hair fixative composition. The hair fixative may consist essentially of the partially-neutralized acrylic polymer solution and additional water.

In other embodiments, the hair fixative compositions may comprise from about 25 to about 77 weight percent water, more preferably from about 35 to 65 weight percent water. The hair fixative compositions may comprise up to 35 weight percent of an organic solvent as discussed herein above, based on the total weight of the hair fixative composition. Preferably the hair fixative composition comprises less than 25 weight percent of the organic solvent, more preferably less than 10 weight percent, based on the total weight of the hair fixative composition. In certain embodiments, the hair fixative composition will be free of organic solvent.

The hair fixative compositions may be in the form of an aerosol or non-aerosol spray, a mousse or a hair-setting lotion. The compositions may contain up to 40 weight percent, preferably up to 35 weight percent, of propellants. In aerosol spray hair fixative compositions, it is preferable to use from about 25 to about 35 weight percent of a propellant. Typical propellants include ethers, compressed gases, halogenated hydrocarbons and hydrocarbons. Exemplary propellants are dimethyl ether, compressed nitrogen, air or carbon dioxide, propane, butane and 1,1-difluoroethane. The hair fixative compositions may further include other materials or additives such as fragrances, preservatives, colorants, plasticizers, emulsifiers, conditioners, neutralizers, glossifiers and the like. Such propellants, organic solvents and materials or additives are commonly used in hair fixative compositions known heretofore.

Mousses according to the present invention further comprise from about 0.25 to 6 weight percent, preferably 0.25 to 3 weight percent, of an emulsifier. The emulsifier may be nonionic, cationic, anionic or amphoteric. Exemplary nonionic emulsifiers include Tergitol® NP 15 (INCI designation—Nonoxynol 15) and Brij 97 (INCI designation—Oleth 10). The mousses also comprise from about 2.5 to 25 weight percent, preferably 5 to 15 weight percent, of a propellant as discussed above. The mousses may comprise additional ingredients as discussed above, with the balance of the mousse comprising water. Optional additives may be incorporated into the hair fixative compositions of the present invention in order to modify certain properties thereof. Among these additives may be included plasticizers such as glycols, phthalate esters and glycerine; silicones; emollients, lubricants and penetrants such as lanolin compounds, protein hydrolyzates and other protein derivatives, ethylene oxide adducts, and polyoxyethylene cholesterol; U.V. absorbers; dyes and other colorants; and perfumes.

The resulting hair fixative compositions of the present invention exhibit all of the characteristics required of a hair fixative. Their films are transparent, glossy, and continuous. They possess good antistatic properties, adhere well to hair, are readily removed by soapy water or shampoos, allow the hair to be readily recombed, do not yellow on aging, do not become tacky when exposed to high humidities, and have excellent curl retention under high humidity conditions.

The following examples are not intended to and should not be construed to limit the scope of the invention, the scope of which is limited only by the claims appended hereto.

Polymer Preparation

An acrylic polymer comprising the residue of about 16 percent of acrylic acid monomer, 40 to 50 percent of a N-alkyl acrylamide monomer and about 30 to 50 percent of a mixture of copolymerizable monomers other than the N-alkyl acrylamide monomer was prepared utilizing standard precipitation polymerization techniques known to those skilled in the art. The polymer powder so prepared was designated Polymer A. All percentages of monomers herein are weight percent based on the total weight of monomers used to prepare the polymers.

A second acrylic polymer comprising the residue of about 10 percent of crotonic acid and about 90 percent of a mixture of vinyl ester monomers was prepared similarly to Polymer A and designated Polymer B.

The polymers were partially-neutralized according to the various conditions set forth in the following examples, thereby preparing the various solutions of partially-neutralized polymers which were evaluated for use in hair fixative compositions. The solvent system used in the neutralization process consisted of water. The partially-neutralized acrylic polymers and solutions thereof were evaluated as discussed herein for clarity/stability in water, pH, clarity/stability in a solvent system consisting of water and EGDME, solution viscosity in the water/EGDME solvent system, film characteristics such as clarity, continuity, i.e., cracking, and redispersibility in water, which relates to removability from hair.

Evaluation Protocol

Appearance of Polymer Solution in Solvent System:

The appearance of a solution of the partially-neutralized polymers in a solvent system consisting of water and EGDME (67/33 weight percent) was visually evaluated for clarity and for homogeneity. Solutions which were hazy to clear and which exhibit no cloudiness, settling, precipitation or phase separation were considered to be viable resins for hair fixative compositions of the present invention.

Evaluation of Films

Film Appearance:

1.5 ml of the homogenous partially-neutralized acrylic polymer solution (5 weight percent polymer solids) was placed into a tin receptacle and dried overnight in a constant temperature/humidity chamber set at 50 percent relative humidity and 23° C. to form a film. The films were visually observed for signs of cracks or other incontinuities in the film.

Redispersibility in Water:

Prescreening shampoo removability of partially-neutralized acrylic polymers was conducted by placing the tin receptacles on dry ice to effect removal of the film from the receptacle. The films formed from the polymer solutions then were placed into about 15 ml of polished water without heating or agitation. Generally, if the film is soluble in water, the film first becomes swollen, becomes gel-like in the water, and finally dissolves in the water. Polymers considered to be viable resins for hair fixatives according to the present invention typically will dissolve within about 10 minutes after being placed in the water. Films which do not dissolve fully in the water but exhibit some degree of redispersability or solubility in water may be used in the hair fixative compositions with some modification of the hair fixative formulations. Films which exhibit no redispersability or solubility in water are not considered to be viable resins for the hair fixatives of the present invention.

Solution Viscosity:

The viscosity of the solution of the partially-neutralized acrylic polymer was determined by preparing a 5 weight percent solution of the partially-neutralized acrylic polymer in a solvent system consisting of 67 weight percent water and 33 weight percent EGDME. The solution viscosity then was measured at 25° C., using a Cannon Capillary Viscometer having a range of from 0 to 50 cp.

EXAMPLE 1

Two-step neutralization vs. One-step neutralization

Properties of homogeneous solutions of partially-neutralized polymers prepared according to the two-step neutralization process of the present invention are compared to polymer solutions prepared by a one-step neutralization process.

One-step Neutralization:

Three comparative solutions of neutralized Polymer A (5% polymer solids) were prepared by combining 2-amino-2-methyl-propanol (at respective molar ratios of base to carboxyl groups contained in Polymer A of 1:1, 0.9:1 and 0.7:1), water and the acrylic polymer to form neutralized polymer solutions. The resulting solutions were evaluated for stability in water and pH.

Two-step Neutralization:

A solution of neutralized acrylic polymer (5% polymer solids) was prepared by combining 2-amino-2-methyl-propanol (at a molar ratio of base to carboxyl groups of 1:1), the acrylic polymer and water. A series of homogeneous solutions of partially-neutralized polymers according to the present invention then was prepared by adding to samples of the solution of neutralized acrylic polymer the various acids, at the various ratios of acid to carboxyl groups contained in the acrylic polymer as set forth in Table 1. The solutions were evaluated as indicated in Table 1.

TABLE 1

| Solution No. | Molar Ratio Base: Carboxyl | Acid | Molar Ratio Acid: Carboxyl | Appearance in $H_2O$ | pH | Appearance in $H_2O$/ EGDME | Viscosity in $H_2O$/ EGDME (cp) | Film Properties | Film Redispersability in $H_2O$ |
| --- | --- | --- | --- | --- | --- | --- | --- | --- | --- |
| 1-1 | 1:1 | — | — | C | 9.15 | | 12.82 | | |
| 1-2 | 0.9:1 | — | — | C | 7.72 | | 11.79 | | |
| 1-3 | 0.7:1 | — | — | C | 6.83 | | 7.87 | | |
| 1-4 | 1:1 | Acetic | 0.2:1 | C | 7.26 | C | 5.58 | C, CON | Y |
| 1-5 | 1:1 | Acetic | 0.4:1 | C | 7.00 | C | 4.27 | SH, CON | P |
| 1-6 | 1:1 | Acetic | 0.5:1 | CL | 6.70 | H | 3.57 | C, CR | N |
| 1-7 | 1:1 | Acetic | 0.6:1 | O | 6.61 | SL | 3.78 | H, CR | N |
| 1-8 | 1:1 | Adipic | 0.4:1 | C | 7.00 | O | 4.27 | H, CON | P |
| 1-9 | 1:1 | Adipic | 0.6:1 | O | 6.63 | H | 3.50 | H—CR | N |
| 1-10 | 1:1 | Succinic | 0.4:1 | C | 6.69 | C | 4.32 | H, CON | Y |
| 1-11 | 1:1 | Succinic | 0.6:1 | H | 6.61 | H | 3.46 | H—CR | N |

LEGEND:
C = clear
SH = slightly hazy
H = hazy
SL = slightly cloudy
CL = cloudy
O = plaque
CON = continuous
CR = cracking
Y = yes
N = no
P = partial As the data in Table 1 indicates, polymer solutions prepared utilizing the two-step neutralization process of the present invention unexpectedly exhibit significantly lower viscosity in water/EGDME than those polymer solutions which were prepared utilizing the one-step neutralization process. For instance, comparative solutions which were neutralized with 2-amino-2-methyl-propanol at respective molar ratios of base to carboxyl groups of 0.9:1 and 0.7:1 (about 90 and 70 mole percent of carboxyl neutralized) exhibited viscosities of 11.79 and 7.87 cp, respectively. However, the inventive solution wherein acid was added to the solution of neutralized acrylic polymer at a molar ratio of 0.2:1 (approximately 80 mole percent of carboxyl groups neutralized) exhibited a viscosity of only 5.58 cp. This surprisingly is well below what the expected viscosity would be for a polymer solution which was neutralized to an equivalent degree using the one-step neutralization method. This aspect of the invention is particularly critical where the partially-neutralized acrylic polymers are utilized in aerosol hair fixatives where viscosity has a critical effect on spray characteristics versus resin on-hair performance characteristics such as hold, humidity resistance and shampoo removability, for example.

EXAMPLE 2

Acid Concentration

In order to avoid permanent precipitation during preparation of the homogeneous solutions of partially-neutralized acrylic polymers according to the present invention, the acid should be added under controlled conditions. The concentration of aqueous solutions of acid and the time period over which the addition of acid are completed are two conditions which may be controlled. If the relative strength of the acid solution is too strong, either due to the use of a relatively strong acid or a relatively high concentration of acid, large droplets of polymer will precipitate due to the local low pH. Such precipitates are usually very difficult to re-dissolve in the solvent system, even after being stirred overnight after addition of the acid.

A homogeneous solution of neutralized Polymer A in water was prepared by combining water, 2-amino-2-methyl-propanol (1:1 molar ratio base to carboxyl groups) and Polymer A (7.5 percent polymer solids). Acetic acid was added to three samples each of the solution of neutralized polymer at a molar ratio of acid to carboxyl groups of 0.3:1. Concentrated acetic acid was added to one sample of the solution of neutralized polymer, while aqueous dilutions of acetic acid were added to each of the two remaining samples of the solution of the neutralized polymer according to Table 2. All acid additions were completed over 25 minutes.

TABLE 2

| Solution No. | Acetic Acid Concentration (Weight %) | Post-Addition Stirring Time To Clear Solution |
|---|---|---|
| 2-1 | 0.7 | 10 min. |
| 2-2 | 1.8 | overnight |
| 2-3 | 100 | permanent precipitate |

As the data in Table 2 indicates, where an aqueous solution of acetic acid of about 0.7 weight percent acetic acid was added over 25 minutes, only 10 minutes of post-addition stirring was required to form a homogeneous, clear solution of the partially-neutralized acrylic polymer. When the acid concentration was increased to about 1.8 weight percent, overnight stirring was required to provide a clear, homogeneous solution of the partially-neutralized acrylic polymer. With no dilution of the acetic acid, a permanent precipitate was formed upon the addition of acid.

EXAMPLE 3

Time of acid addition

Slow addition of the acid may be required to avoid permanent precipitation when preparing the homogeneous solutions of the partially-neutralized acrylic polymers. The stronger the acid, the slower the acid addition is completed. The time of acid addition is adjusted such that there are no large droplets of precipitate formed during polymer solution preparation. However, some tiny fiber-like precipitate may form, in which case additional post-addition stirring may be required to provide the clear, homogeneous solution of partially-neutralized acrylic polymer. Weak acids are preferred to avoid low local pH (which causes polymer precipitation) and to accelerate the process.

3A. A series of homogeneous solutions of partially-neutralized acrylic Polymer A (7.5 weight percent polymer solids) in water was prepared by first neutralizing Polymer A with 2-amino-2-methyl-propanol (1:1 base:carboxyl molar ratio) and then adding a 1.8 weight percent aqueous acetic acid solution (0.3:1 acid:carboxyl molar ratio) over the period of time noted in Table 3A. The solutions were stirred overnight after acid addition and the appearance of the solution was noted in Table 3A.

TABLE 3A

| Solution | Acid Addition Time (min) | Appearance Post-stirring |
|---|---|---|
| 3A-1 | 30 | C |
| 3A-2 | 25 | C |
| 3A-3 | 10 | some undissolved solids |
| 3A-4 | 7 | some undissolved solids |

3B. A second series of solutions of partially-neutralized Polymer A (7.5 weight percent polymer solids) was prepared as above, except that the acid added, the concentration of acid added and time of acid addition were varied as set forth in Table 3B. All acids were added to the respective solutions of neutralized Polymer A at a molar ratio of acid to carboxyl groups contained in Polymer A of 0.3:1. Each solution was stirred for an additional 30 minutes after addition of acid was completed.

TABLE 3B

| Solution No. | Acid | Acid Concentration (weight %) | Acid Addition time (min.) |
|---|---|---|---|
| 3B-1 | Propionic | 0.9 | 15 |
| 3B-2 | Butyric | 1.1 | 15 |
| 3B-3 | Phosphoric | 0.4 | 10 |
| 3B-4 | Nitric | 0.8 | 35 |
| 3B-5 | Hydrochloric | 1.2 | 35 |
| 3B-6 | Sulfuric | 0.6 | 45 |

EXAMPLE 4

A series of solutions of partially-neutralized Polymer A (5 weight percent polymer solids) was prepared as in Example 3, with the acid, acid concentration, time of acid addition and post-addition stirring being varied as set forth in Table 4. All solutions of partially-neutralized acrylic polymers so prepared yielded clear, homogeneous solutions.

TABLE 4

| Solution No. | Acid | Acid Concentration (weight %) | Acid Addition time (min.) | Post-Addition Stirring |
|---|---|---|---|---|
| 4-1 | Acetic | 0.7 | 25 | 10 min. |
| 4-2 | Acetic | 1.8 | 25 | overnight |
| 4-3 | Nitric | 0.8 | 35 | 30 min. |
| 4-4 | Hydrochloric | 1.2 | 35 | 30 min. |
| 4-5 | Phosphoric | 0.4 | 10 | 30 min. |
| 4-6 | Sulfuric | 0.6 | 45 | 30 min. |
| 4-7 | Butyric | 1.1 | 15 | 30 min. |
| 4-8 | Proprionic | 0.9 | 15 | 30 min. |

EXAMPLE 5

A series of solutions of Polymer A at 5 weight percent polymer solids was prepared according to processes of the present invention. Polymer A first was neutralized with 2-amino-2-methyl-propanol (1:1 molar ratio base:carboxyl) and then acid was added (0.3:1 molar ratio acid:carboxyl) under conditions of concentration and time of addition which were effective to provide clear, homogeneous solutions of the partially-neutralized polymers. The solutions were evaluated for clarity/stability in $H_2O$, pH, clarity/stability in $H_2O$/EGDME and viscosity in $H_2O$/EGDME. Results are set forth in Table 5.

TABLE 5

| Solution No. | Acid | Appearance in $H_2O$ | pH | Appearance in $H_2O$/EGDME | Viscosity in $H_2O$ EGDME (cp) |
| --- | --- | --- | --- | --- | --- |
| 5-1 | Acetic | C | 7.06 | C | 5.79 |
| 5-2 | Nitric | C | 6.95 | C | 5.50 |
| 5-3 | Hydrochloric | C | 7.04 | C | 5.89 |
| 5-4 | Phosphoric | C | 7.61 | C | 10.02 |
| 5-5 | Sulfonic | C | 7.04 | C | 6.40 |
| 5-6 | Butyric | C | 7.10 | C | 6.22 |
| 5-7 | Propionic | C | 6.97 | C | 5.63 |

EXAMPLE 6

A series of solutions of partially-neutralized Polymer B (5 weight percent polymer solids) was prepared first by combining Polymer B, water and 2-amino-2-methyl-propanol (1:1 base:carboxyl) to form the neutralized solution of Polymer B in water. Acetic acid was added to each of three samples of the solution of neutralized Polymer B under conditions of acid concentration and time of acid addition which were effective to provide the homogeneous solutions of partially-neutralized Polymer B and at the acid:carboxyl molar ratio indicated in Table 6. The solutions of partially-neutralized Polymer B were evaluated for clarity/stability in $H_2O$, pH, clarity/stability in $H_2O$/EGDME, viscosity in $H_2O$/EGDME, film formation and film redispersability in $H_2O$. Results are set forth in Table 6.

TABLE 6

| Solution No. | Molar Ratio Acid:Carboxyl | Appearance in $H_2O$ | pH | Appearance in $H_2O$/EGDME | Viscosity in $H_2O$/EGDME (cp) | Film Properties | Film Redispersability in $H_2O$ |
| --- | --- | --- | --- | --- | --- | --- | --- |
| 6-1 | 0.2:1 | SL | 7.1 | SH | 5.31 | C—CON | Y |
| 6-2 | 0.3:1 | SL | 6.9 | SH | 4.73 | C—CON | Y |
| 6-3 | 0.4:1 | SL | 6.7 | CL | 3.90 | C—CON | N |

We claim:

1. A method of preparing a homogeneous solution of a partially-neutralized acrylic polymer in a solvent system, said solution being suitable for use in acrylic hair fixative compositions, the method comprising:

combining a solvent system which comprises water and optionally an organic solvent at levels of greater than 50 weight percent water, based on total weight of the water and the organic solvent, and 0 to less than 50 weight percent of the organic solvent, based on total weight of the water and the organic solvent, an acrylic polymer which is insoluble in the solvent system and which is suitable for use in a hair fixative composition, and a neutralizing base in amounts effective to neutralize the acrylic polymer to the extent that the neutralized acrylic polymer is soluble in the solvent system, thereby forming a homogenous solution of the neutralized acrylic polymer in the solvent system, which solution has a pH of about 7 or greater; and adding to the homogeneous solution of the neutralized acrylic polymer a water-soluble acid in amounts effective to provide a solution of a partially-neutralized acrylic polymer in the solvent system, which solution of partially-neutralized acrylic polymer has a pH which is lower than the pH of the solution of the neutralized acrylic polymer and a viscosity which is less than the viscosity of the solution of the neutralized acrylic polymer, wherein the addition of the acid is conducted under conditions effective to provide the homogeneous solution of the partially-neutralized acrylic polymer and wherein the pH and the viscosity of the solution of the partially-neutralized acrylic polymer are effective for use in the acrylic hair fixative composition.

2. The method of claim 1 wherein the acrylic polymer comprises the residue of from 0 to about 60 weight percent of a monomer selected from the group consisting of N-substituted acrylamide and N-substituted methacrylamide, from about 8 to about 25 weight percent of an acidic monomer selected from the group consisting of acrylic acid, methacrylic acid, crotonic acid, itaconic acid, maleic acid, fumaric acid, the $C_1$–$C_4$ alkyl half esters of maleic acid and the $C_1$–$C_4$ alkyl half esters of fumaric acid, and from 0 to 90 weight percent of a copolymerizable monomer other than the N-subsituted acrylamide and N-substiuted methacrylamide, all weight percents being based on the total weight of monomers used to prepare the acrylic polymer.

3. The method of claim 1 wherein the acrylic polymer comprises the residue of from about 10 to about 22 weight percent of an acidic monomer selected from the group consisting of acrylic acid, methacrylic acid, crotonic acid, itaconic acid, maleic acid, fumaric acid, the $C_1$–$C_4$ alkyl half esters of maleic acid and the $C_1$–$C_4$ alkyl half esters of fumaric acid, from about 35 to about 55 weight percent of a monomer selected from the group consisting of an N-alkyl acrylamide and an N-alkyl methacrylamide and from about 25 to about 80 percent of a copolymerizable monomer other than the N-alkyl acrylamide and N-alkyl methacrylamide, all weight percents being based on the total weight of monomers used to prepare the acrylic polymer.

4. The method of claim 2 wherein the effective amount of the neutralizing base is a molar ratio of base to carboxyl groups contained in the acrylic polymer greater than or equal to 0.9:1 and the effective amount of acid is a molar ratio of acid to the carboxyl groups contained in the acrylic polymer greater than or equal to 0.1:1.

5. The method of claim 2 wherein the effective amount of the neutralizing base is a molar ratio of base to carboxyl groups contained in the acrylic polymer of from about 0.9:1 to about 2:1 and the effective amount of acid is a molar ratio of acid to the carboxyl groups contained in the acrylic polymer of from about 0.1:1 to about 2.0:1.

6. The method of claim 2 wherein the effective amount of the neutralizing base is a molar ratio of base to carboxyl groups contained in the acrylic polymer of from about 1:1 to about 1.5:1 and the effective amount of acid is a molar ratio of acid to the carboxyl groups contained in the acrylic polymer of from about 0.2:1 to about 0.8:1.

7. The method of claim 1 wherein the solvent system contains greater than 60 weight percent of the water.

8. The method of claim 1 wherein the solvent system contains greater than 75 weight percent of the water.

9. The method of claim 1 wherein the solvent system consists essentially of water.

10. The method of claim 1 wherein the solvent system consists of water.

11. The method of claim 1 wherein the homogenous solution of the partially-neutralized acrylic polymer contains from about 1 to about 20 weight percent of the partially-neutralized acrylic polymer.

12. The method of claim 1 wherein the homogeneous solution of the partially-neutralized acrylic polymer contains from about 2 to about 15 weight percent of the partially-neutralized acrylic polymer.

13. The method of claim 1 wherein the neutralizing base is selected from the group consisting of sodium hydroxide, potassium hydroxide, ammonia, primary, secondary and tertiary amines, alkanolamines and hydroxyamines.

14. The method of claim 1 wherein the acid is selected from the group consisting of inorganic acids and organic acids.

15. The method of claim 1 wherein the acid is diluted in water to a concentration effective to provide the homogeneous solution of the partially-neutralized acrylic polymer prior to the addition thereof to the solution of the neutralized acrylic polymer.

16. The method of claim 1 wherein the acid is added over a period of time which is effective to provide the homogeneous solution of the partially-neutralized acrylic polymer.

17. The method of claim 15 wherein the acid is added over a period of time which is effective to provide the homogeneous solution of the partially-neutralized acrylic polymer.

18. The method of claim 1 wherein the organic solvent is selected from the group consisting of ethanol, isopropanol, acetone, ethylene glycol dimethyl ether and methyl ethyl ketone.

19. The method of claim 1 wherein the homogeneous solution of the partially-neutralized acrylic polymer has a viscosity of from about 2 cp to about 10 cp.

20. The method of claim 1 wherein the pH of the homogeneous solution of the partially-neutralized acrylic polymer ranges from about 5.5 to about 8.5.

21. The method of claim 19 wherein the pH of the homogeneous solution of the partially-neutralized acrylic polymer ranges from 6.0 to 8.0.

22. The method of claim 1 wherein the pH of the homogeneous solution of the partially-neutralized acrylic polymer is about 7 and the viscosity of the homogeneous solution of the partially-neutralized acrylic polymer ranges from about 2 cp and about 7 cp.

23. The homogeneous solution of a partially-neutralized acrylic polymer prepared according to the method of claim 1.

24. The homogeneous solution of a partially-neutralized acrylic polymer prepared according to the method of claim 4.

25. The homogeneous solution of a partially-neutralized acrylic polymer prepared according to the method of claim 17.

26. A method for preparing an acrylic hair fixative composition, the method comprising:

combining a solvent system which comprises water and optionally an organic solvent at levels of greater than 50 weight percent water, based on total weight of the water and the organic solvent, and 0 to less than 50 weight percent of the organic solvent, based on total weight of the water and the organic solvent, an acrylic polymer which is insoluble in the solvent system and which is suitable for use in a hair fixative composition, and a neutralizing base in amounts effective to neutralize the acrylic polymer to the extent that the neutralized acrylic polymer is soluble in the solvent system, thereby forming a homogenous solution of the neutralized acrylic polymer in the solvent system, which solution has a pH of about 7 or greater, adding to the homogeneous solution of the neutralized acrylic polymer an acid in amounts effective to provide a solution of a partially-neutralized acrylic polymer in the solvent system, which solution of partially-neutralized acrylic polymer has a pH which is lower than the pH of the solution of the neutralized acrylic polymer and a viscosity which is less than the viscosity of the solution of the neutralized acrylic polymer, wherein the addition of the acid is conducted under conditions effective to provide the homogeneous solution of the partially-neutralized acrylic polymer and wherein the pH and the viscosity of the solution of the partially-neutralized acrylic polymer are effective for use in the acrylic hair fixative composition; and combining with the solution of the partially-neutralized acrylic polymer water, 0 to 40 weight percent of a propellant, and 0 to 15 weight percent of an emulsifier, thereby forming the acrylic hair fixative composition, wherein the acrylic hair fixative composition comprises from about 3 to about 10 dry weight percent of the partially-neutralized acrylic polymer and from about 25 to about 97 weight percent of the water, wherein the respective weight percents of the propellant, the emulsifier, the partially-neutralized acrylic polymer and the water are based on the total weight of the hair fixative composition.

27. The method of claim 26 wherein the acrylic polymer comprises the residue of from 0 to about 60 weight percent of a monomer selected from the group consisting of N-substituted acrylamide and N-substituted methacrylamide, from about 8 to about 25 weight percent of an acidic monomer selected from the group consisting of acrylic acid, methacrylic acid, crotonic acid, itaconic acid, maleic acid, fumaric acid, the $C_1$–$C_4$ alkyl half esters of maleic acid and the $C_1$–$C_4$ alkyl half esters of fumaric acid, and from 0 to about 90 weight percent of a copolymerizable monomer other than the N-substituted acrylamide and N-substituted methacrylamide, all weight percents being based on the total weight of monomer used to prepare the acrylic polymer.

28. The method of claim 26 wherein the acrylic polymer comprises the residue of from about 10 to about 22 weight percent of an acidic monomer selected from the group consisting of acrylic acid, methacrylic acid, crotonic acid, itaconic acid, maleic acid, fumaric acid, the $C_1$–$C_4$ alkyl half esters of maleic acid and the $C_1$–$C_4$ alkyl half esters of fumaric acid, from about 35 to about 55 weight percent of a monomer selected from the group consisting of an N-alkyl acrylamide and an N-alkyl methacrylamide and from about 25 to about 80 percent of a copolymerizable monomer other than the N-alkyl acrylamide and N-alkyl methacrylamide, all weight percents being based on the total weight of monomers used to prepare the acrylic polymer.

29. The method of claim 27 wherein the effective amount of the neutralizing base is a molar ratio of base to carboxyl groups contained in the acrylic polymer greater than or equal to 0.9:1 and the effective amount of acid is a molar ratio of acid to the carboxyl groups contained in the acrylic polymer greater than or equal to 0.1:1.

30. The method of claim 27 wherein the effective amount of the neutralizing base is a molar ratio of base to carboxyl groups contained in the acrylic polymer of from about 0.9:1 to about 2:1 and the effective amount of acid is a molar ratio of acid to the carboxyl groups contained in the acrylic polymer of from about 0.1:1 to about 1.5:1.

31. The method of claim 27 wherein the effective amount of the neutralizing base is a molar ratio of base to carboxyl groups contained in the acrylic polymer of from about 1:1 to about 1.5:1 and the effective amount of acid is a molar ratio of acid to the carboxyl groups contained in the acrylic polymer of from about 0.2:1 to about 0.8:1.

32. The method of claim 26 wherein the solvent system contains greater than 60 weight percent of the water.

33. The method of claim 26 wherein the solvent system contains greater than 75 weight percent of the water.

34. The method of claim 26 wherein the solvent system consists essentially of water.

35. The method of claim 26 wherein the solvent system consists of water.

36. The method of claim 26 wherein the homogenous solution of the partially-neutralized acrylic polymer contains from about 1 to about 20 weight percent of the partially-neutralized acrylic polymer.

37. The method of claim 26 wherein the homogeneous solution of the partially-neutralized acrylic polymer contains from about 2 to about 15 weight percent of the partially-neutralized acrylic polymer.

38. The method of claim 26 wherein the neutralizing base is selected from the group consisting of sodium hydroxide, potassium hydroxide, ammonia, primary, secondary and tertiary amines, alkanolamines and hydroxyamines.

39. The method of claim 26 wherein the acid is selected from the group consisting of inorganic acids and organic acids.

40. The method of claim 26 wherein the acid is diluted in water to a concentration effective to provide the homogeneous solution of the partially-neutralized acrylic polymer prior to the addition thereof to the solution of the neutralized acrylic polymer.

41. The method of claim 26 wherein the acid is added over a period of time which is effective to provide the homogeneous solution of the partially-neutralized acrylic polymer.

42. The method of claim 40 wherein the acid is added over a period of time which is effective to provide the homogeneous solution of the partially-neutralized acrylic polymer.

43. The method of claim 26 wherein the organic solvent is selected from the group consisting of ethanol, isopropanol, acetone, ethylene glycol dimethyl ether and methyl ethyl ketone.

44. The method of claim 26 wherein the homogeneous solution of the partially-neutralized acrylic polymer has a viscosity of from about 2 cp to about 10 cp.

45. The method of claim 26 wherein the pH of the homogeneous solution of the partially-neutralized acrylic polymer ranges from about 5.5 to about 8.5.

46. The method of claim 44 wherein the pH of the homogeneous solution of the partially-neutralized ranges from 6.0 to 8.0.

47. The method of claim 26 wherein the pH of the homogeneous solution of the partially-neutralized acrylic polymer is about 7 and the viscosity of the homogeneous solution of the partially-neutralized acrylic polymer ranges from about 2 cp and about 7 cp.

48. The method of claim 26 wherein the hair fixative composition comprises less than 25 weight percent of the organic solvent.

49. The method of claim 26 wherein the hair fixative composition comprises from about 35 to about 65 weight percent of the water and less than 25 weight percent of the organic solvent.

50. The method of claim 26 wherein the hair fixative composition comprises less than 10 weight percent of the organic solvent.

51. The method of claim 26 wherein the hair fixative composition is free of the organic solvent.

52. The hair fixative composition prepared according to the method of claim 26.

53. The hair fixative composition prepared according to the method of claim 29.

54. The hair fixative composition prepared according to the method of claim 42.

55. A hair fixative composition, comprising:
a homogenous solution of a partially-neutralized acrylic polymer which is suitable for use in a hair fixative composition in an amount effective for use in the hair fixative composition,
from about 25 to about 97 weight percent of water,
0 to 40 weight percent of a propellant,
0 to 15 weight percent of an emulsifier; and
0 to 35 weight percent of an organic solvent,
wherein the respective weight percents of the water, the propellant, the emulsifier and the organic solvent are based on the total weight of the hair fixative composition, the hair fixative composition characterized in that the homogenous solution of the partially-neutralized acrylic polymer was prepared by,
combining a solvent system which comprises water and optionally an organic solvent at levels of greater than 50 weight percent water, based on total weight of the water and the organic solvent, and 0 to less than 50 weight percent of the organic solvent, based on total weight of the water and the organic solvent, an acrylic polymer which is insoluble in the solvent system and which is suitable for use in a hair fixative composition, and a neutralizing base in amounts effective to neutralize the acrylic polymer to the extent that the neutralized acrylic polymer is soluble in the solvent system, thereby forming a homogenous solution of the neutralized acrylic polymer in the solvent system, which solution has a pH of about 7 or greater; and
adding to the homogeneous solution of the neutralized acrylic polymer an acid in amounts effective to provide a solution of the partially-neutralized acrylic polymer in the solvent system, which solution of partially-neutralized acrylic polymer has a pH which is lower than the pH of the solution of the neutralized acrylic polymer and a viscosity which is less than the viscosity of the solution of the neutralized acrylic polymer, wherein the addition of the acid is conducted under conditions effective to provide the homogeneous solution of the partially-neutralized acrylic polymer and wherein the pH and the viscosity of the solution of the partially-neutralized acrylic polymer are effective for use in the acrylic hair fixative composition.

56. The hair fixative composition of claim 55 wherein the acrylic polymer comprises the residue of from 0 to about 60 weight percent of a monomer selected from the group consisting of N-substituted acrylamide and N-substituted methacrylamide, from about 8 to about 25 weight percent of an acidic monomer selected from the group consisting of acrylic acid, methacrylic acid, crotonic acid, itaconic acid, maleic acid, fumaric acid, the $C_1$–$C_4$ alkyl half esters of maleic acid and the $C_1$–$C_4$ alkyl half esters of fumaric acid, and from 0 to about 90 weight percent of a copolymerizable monomer other than the N-substituted acrylamide and N-substituted methacrylamide, all weight percents being based on the total weight of monomer used to prepare the acrylic polymer.

57. The hair fixative composition of claim 55 wherein the acrylic polymer comprises the residue of from about 10 to about 22 weight percent of an acidic monomer selected from the group consisting of acrylic acid, methacrylic acid, crotonic acid, itaconic acid, maleic acid, fumaric acid, the $C_1$–$C_4$ alkyl half esters of maleic acid and the $C_1$–$C_4$ alkyl half esters of fumaric acid, from about 35 to about 55 weight percent of a monomer selected from the group consisting of an N-alkyl acrylamide and an N-alkyl methacrylamide and from about 25 to about 80 percent of a copolymerizable monomer other than the N-alkyl acrylamide and N-alkyl methacrylamide, all weight percents being based on the total weight of monomers used to prepare the acrylic polymer.

58. The hair fixative composition of claim 56 wherein the effective amount of the neutralizing base is a molar ratio of base to carboxyl groups contained in the acrylic polymer greater than or equal to 0.9:1 and the effective amount of acid is a molar ratio of acid to the carboxyl groups contained in the acrylic polymer greater than or equal to 0.1:1.

59. The hair fixative composition of claim 57 wherein the effective amount of the neutralizing base is a molar ratio of base to carboxyl groups contained in the acrylic polymer of from about 0.9:1 to about 2:1 and the effective amount of acid is a molar ratio of acid to the carboxyl groups contained in the acrylic polymer of from about 0.1:1 to about 1.5:1.

60. The hair fixative composition of claim 56 wherein the effective amount of the neutralizing base is a molar ratio of base to carboxyl groups contained in the acrylic polymer of from about 1:1 to about 1.5:1 and the effective amount of acid is a molar ratio of acid to the carboxyl groups contained in the acrylic polymer of from about 0.2:1 to about 0.8:1.

61. The hair fixative composition of claim 55 wherein the solvent system contains greater than 60 weight percent of the water.

62. The hair fixative composition of claim 55 wherein the solvent system contains greater than 75 weight percent of the water.

63. The hair fixative composition of claim 55 wherein the solvent system consists essentially of water.

64. The hair fixative composition of claim 55 wherein the solvent system consists of water.

65. The hair fixative composition of claim 55 wherein the organic solvent is selected from the group consisting of ethanol, isopropanol, acetone, ethylene glycol dimethyl ether and methyl ethyl ketone.

66. The hair fixative composition of claim 55 wherein the homogeneous solution of the partially-neutralized acrylic polymer has a viscosity of from about 2 cp to about 10 cp.

67. The hair fixative composition of claim 55 wherein the pH of the homogeneous solution of the partially-neutralized acrylic polymer ranges from about 5.5 to about 8.5.

68. The hair fixative composition of claim 55 wherein the hair fixative composition comprises less than 25 weight percent of the organic solvent, based on the total weight of the hair fixative composition.

69. The hair fixative composition of claim 55 wherein the hair fixative composition comprises from about 35 to about 65 weight percent of the water and less than 25 weight percent of the organic solvent, wherein the respective weight percents of the water and the organic solvent are based on the total weight of the hair fixative composition.

70. The hair fixative composition of claim 55 wherein the hair fixative composition comprises less than 10 weight percent of the organic solvent, based on the total weight of the hair fixative composition.

71. The hair fixative composition of claim 55 wherein the hair fixative composition is free of the organic solvent.

72. The hair fixative composition of claim 55 comprising from about 3 to about 10 dry weight percent of the partially-neutralized acrylic polymer, based on the total weight of the hair fixative composition.

\* \* \* \* \*